(12) United States Patent
Khatun et al.

(10) Patent No.: US 10,765,617 B2
(45) Date of Patent: Sep. 8, 2020

(54) PERSONAL CARE COMPOSITIONS COMPRISING COPOLYMERS OF CATIONIC MONOMERS AND ACRYLOYL LACTAM BASED MONOMERS, PROCESS FOR THE SAME AND METHOD OF USE

(71) Applicant: ISP INVESTMENTS LLC, Wilmington, DE (US)

(72) Inventors: Amna Khatun, West Yorkshire (GB); David Petty, Bradford (GB); Lidia Kulcsar, Flanders, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 15/772,686

(22) PCT Filed: Nov. 21, 2016

(86) PCT No.: PCT/US2016/062994
§ 371 (c)(1),
(2) Date: May 1, 2018

(87) PCT Pub. No.: WO2017/087924
PCT Pub. Date: May 26, 2017

(65) Prior Publication Data
US 2019/0151224 A1    May 23, 2019

Related U.S. Application Data

(60) Provisional application No. 62/257,761, filed on Nov. 20, 2015.

(51) Int. Cl.
| | | |
|---|---|---|
| *A61Q 5/02* | (2006.01) | |
| *A61Q 5/06* | (2006.01) | |
| *A61K 8/81* | (2006.01) | |
| *C08F 220/18* | (2006.01) | |
| *C08F 226/10* | (2006.01) | |
| *A61Q 5/12* | (2006.01) | |
| *A61Q 1/02* | (2006.01) | |

(52) U.S. Cl.
CPC ............ *A61K 8/8182* (2013.01); *A61K 8/817* (2013.01); *A61Q 5/02* (2013.01); *A61Q 5/06* (2013.01); *A61Q 5/12* (2013.01); *C08F 220/18* (2013.01); *C08F 226/10* (2013.01); *A61K 2800/5426* (2013.01); *A61K 2800/95* (2013.01); *A61Q 1/02* (2013.01)

(58) Field of Classification Search
None
See application file for complete search history.

(56) References Cited

U.S. PATENT DOCUMENTS

| | | | |
|---|---|---|---|
| 4,767,613 A | 8/1988 | Nuber et al. | |
| 5,997,855 A | 12/1999 | Liu | |
| 2009/0197791 A1* | 8/2009 | Balastre | A61K 8/8158 510/407 |
| 2015/0005465 A1 | 1/2015 | Hood et al. | |
| 2015/0297496 A1* | 10/2015 | Kroon | A61Q 5/06 424/54 |

FOREIGN PATENT DOCUMENTS

| | | |
|---|---|---|
| WO | WO9314024 A1 | 7/1993 |
| WO | WO2014071354 * | 5/2014 |

OTHER PUBLICATIONS

Definition of Copolymer, dictionary.com, https://www.dictionary.com/browse/copolymer, retrieved online on Feb. 18, 2020 (Year: 2020).*
International Search Report, PCT/US2016/062994 published on May 26, 2017.

* cited by examiner

*Primary Examiner* — Jennifer A Berrios
(74) *Attorney, Agent, or Firm* — William J. Davis; Nathalie Tietcheu

(57) ABSTRACT

Disclosed herein is a personal care conditioning and/or styling composition for keratin substrate comprising: (A) at least one conditioning and/or styling copolymer obtained from polymerizing: (i) about 0.1 wt. % to 99.9 wt. % of at least one cationic or pseudo-cationic monomer selected from the group consisting of acrylamidopropyl trimethylammonium chloride (APTAC) and/or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety; (B) at least one cosmetically acceptable excipient; and (C) optionally, at least one effective amount of personal care active ingredient. Also disclose is a process for preparing such composition and method of use thereof.

4 Claims, 3 Drawing Sheets

PERSONAL CARE COMPOSITIONS COMPRISING COPOLYMERS OF CATIONIC MONOMERS AND ACRYLOYL LACTAM BASED MONOMERS, PROCESS FOR THE SAME AND METHOD OF USE

FIELD OF THE INVENTION

The present application provides a conditioning and/or styling composition copolymer comprising cationic monomers and monomers having at least one functionalized or unfunctionalized acryloyl lactam based moiety.

BACKGROUND OF THE INVENTION

Undamaged virgin hair is smooth and shiny; its cuticles on the surface of the hair lie down smoothly making the combing easy. The hair surface is also hydrophobic in nature preventing excessive water absorption during washing. When the hair is either mechanically damaged through back combing, heavy brushing, or chemically damaged through bleaching, perming or coloring, the hair surface becomes rough and frizzy and difficult to detangle and comb. As the hair surface becomes more hydrophilic, the resulting hair fibers swell during washing, making the hair even more difficult to comb.

Current conditioning and/or styling systems for regular and damaged hair generally use one or more combinations of cationic surfactants, amphoteric surfactants, silicones, fatty alcohols, polyquaterniums, amino acids, proteins, lipids and humectants. Wet conditioning of regular or damaged hair is accomplished by neutralizing the anionic charge of the hair by positively charged surfactants and polymers and creating a hydrophobic layer from surfactant and polymers. This hydrophobic layer results in a reduction of the swelling of the hair fibers by making the hair more hydrophobic and smoothening the cuticle layers thus and reducing friction of the hair fibers. An overall result of wet conditioning is improved detangling, manageability and soft feel of the hair. Upon treatment with cleansing systems like shampoos, 2/1 shampoos, body washes or shower gels, the combing performance, detangling properties, hydrophobicity of the hair and lubricity are not maintained sufficiently.

PCT application No. 2014/071354 assigned to Hercules discloses a personal care conditioning and/or styling composition for a keratin substrate comprising: (i) about 50 wt. % to 95 wt. % of at least one cationic or pseudo-cationic monomer selected from the group consisting of acrylamidopropyl trimethylammonium chloride (APTAC) and/or Vinylpyrrolidone (VP); (ii) about \ wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene (PEG)-18-behenylether-methacrylate (BEM) (b) Lauryl-ethoxylated-methacrylate (LEM), (c) stearyl acrylate (SA), (d) Stream-10-allyl-ether, (e) Vinylcaprolactam (V-cap), and/or (f) Hydroxyethyl-pyrrolidone-methacrylate.

U.S. Pat. No. 6,110,451 assigned to Calgon discloses a conditioning composition comprising: (a) about 5% to about 50%, by weight, of a surfactant component selected from the group consisting of anionic surfactants, amphoteric surfactants, cationic surfactants, nonionic surfactants, and zwitterionic surfactants; (b) about 0.05% to about 10%, by weight; of a water soluble, organic, ampholytic polymer conditioning agent (c) about 0.05% to about 10%, by weight, of a water soluble, organic, cationic polymer conditioning agent; (d) zero to about 70%, by weight, of a water insoluble liquid; and (e) an aqueous carrier wherein said ampholytic polymer conditioning agent of (b) is comprised of (A) at least one ethylenically unsaturated cationic monomer and (B) at least one ethylenically unsaturated acid containing monomer.

US Publication No. 20150053361 assigned to S.P.C.M.SA disclose a polymer complex obtained by polymerization of water-soluble monomers in the presence of a host polymer comprising vinylamine functions and of a non-polymeric transfer agent, and in the absence of branching or crosslinking agent of ethylenic polyfunctional type.

In view of the foregoing, there is an increasing demand for hair care products designed to retain the properties of "virgin hair" and to prevent possible damage during the chemical and mechanical treatment. In the present application, the limitations set forth above are addressed by a personal care conditioning and/or styling composition for a keratin substrate comprising: (A) at least one conditioning and/or styling copolymer obtained by polymerizing (i) about 0.1 wt. % to 99.9 wt. % of at least one cationic or pseudo-cationic monomer selected from the group consisting of acrylamidopropyl trimethylammonium chloride (APTAC) and/or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety; (B) at least one cosmetically acceptable excipient; and optionally, at least one effective amount of personal care active ingredient

SUMMARY OF THE INVENTION

The present application provides a personal care conditioning and/or styling composition for a keratin substrate comprising: (A) at least one conditioning and/or styling copolymer obtained by polymerizing (i) about 0.1 wt. % to 99.9 wt. % of at least one cationic or pseudo-cationic monomer selected from the group consisting of acrylamidopropyl trimethylammonium chloride (APTAC) and/or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety; (B) at least one cosmetically acceptable excipient; and optionally, at least one effective amount of personal care active ingredient.

An important embodiment of the present application is to provide a conditioning and/or styling copolymer for a keratin substrate having a cationic degree of substitution (Cat-DS) of greater than about 0.001 units, and wherein the cationic charge density is in the range of about 1 meq/g to about 6 meq/g.

According to one another aspect of the present application, the hair care composition comprising the above-described copolymer is capable of providing long lasting conditioning effect even after 3 or more non-conditioning shampoo based hair washings.

Yet another aspect of the present application is to provide a method for washing or caring for a keratin substrate comprising applying an effective amount of composition comprising (a) a conditioning and/or styling copolymer (i) about 0.1 wt. % to 99.9 wt. % of acrylamidopropyl trimethylammonium chloride (APTAC) or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety wherein said copolymer has a cationic degree of substitution (Cat-DS) of greater than about 0.001 units, and wherein the cationic charge density is in the range of about 1 meq/g to about 6 meq/g.

Still another aspect of the present application is to provide a process for preparing a conditioning and/or styling copolymer comprising polymerizing (i) about 0.1 wt. % to 99.9 wt. % of acrylamidopropyl trimethylammonium chloride (APTAC) or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety, wherein the prepared copolymer has a cationic degree of substitution (Cat-DS) of greater than about 0.001 units, and wherein the cationic charge density is in the range of about 1 meq/g to about 6 meq/g.

BRIEF DESCRIPTION OF THE FIGURES

Further embodiments of the present application can be understood with the appended figures.

DETAILED DESCRIPTION OF THE INVENTION

Figure 1:
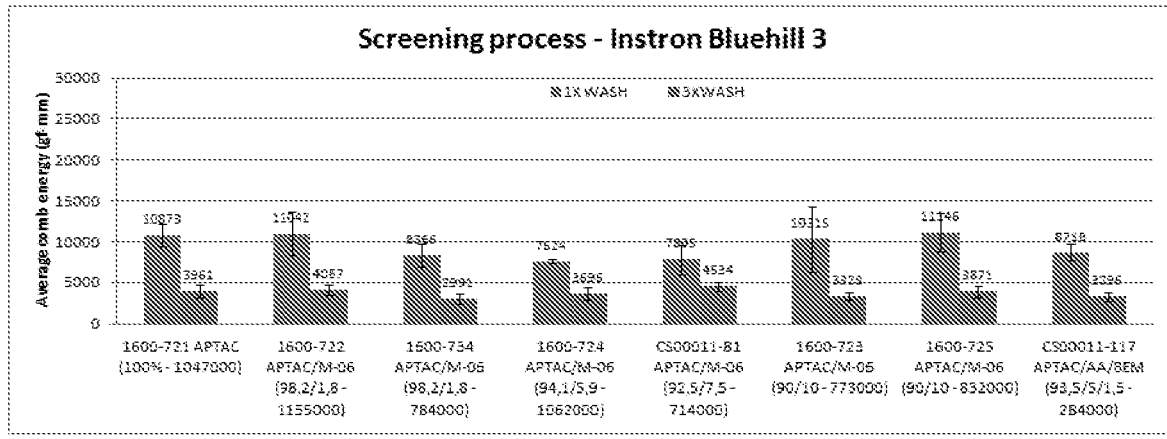
FIG. 1 depicts wet comb energy evaluation for various copolymers APTAC/Pyrrolidonylethyl methacrylate (PyEMA) in different ratio.

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description or illustrated in the drawings. The disclosed and/or claimed inventive concept(s) is capable of other aspects or of being practiced or carried out in various ways. Also, it is to be understood that the phraseology and terminology employed herein is for the purpose of description and should not be regarded as limiting.

As utilized in accordance with the disclosure, the following terms, unless otherwise indicated, shall be understood to have the following meanings.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

The term "about" can indicate a difference of 10 percent of the value specified. Numerical ranges as used herein are meant to include every number and subset of numbers enclosed within that range, whether particularly disclosed or not. Further, these numerical ranges should be construed as providing support for a claim directed to any number or subset of numbers in that range.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

As used herein, the words "preferred" or "preferably" and variants refer to embodiments of the application that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the application.

References herein to "one embodiment" or "one aspect" or "one version" or "one objective" of the application include one or more such embodiment, aspect, version or objective, unless the context clearly dictates otherwise.

All publications, articles, papers, patents, patent publications, and other references cited herein are hereby incorporated herein in their entirety for all purposes to the extent consistent with the disclosure herein.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "each independently selected from the group consisting of" means when a group appears more than once in a structure, that group may be selected independently each time it appears.

The term "polymer" refers to a compound comprising repeating structural units (monomers) connected by covalent chemical bonds. Polymers may be further derivatized, cross-linked, grafted or end-capped. Non-limiting examples of polymers include copolymers, terpolymers, tetrapolymers, quaternary polymers, and homologues. The term "copolymer" refers to a polymer consisting essentially of two or more different types of monomers polymerized to obtain said copolymer.

The term "alkyl" refers to a functionalized or unfunctionalized monovalent straight-chain, branched-chain or cyclic $C_1$-$C_{60}$ group optionally having one or more heteroatoms. Particularly, an alkyl is a $C_1$-$C_{45}$ group and more particularly, a $C_1$-$C_{30}$ group. Particular, yet non-limiting examples of alkyl groups include methyl, ethyl, n-propyl, isopropyl, n-butyl, isobutyl, tert-butyl, cyclobutyl, n-pentyl, isopentyl, cyclopentyl, n-hexyl, cyclohexyl, n-heptyl, cycloheptyl, methylcyclohexyl, n-octyl, 2-ethylhexyl, tert-octyl, iso-norbornyl, n-dodecyl, tert-dodecyl, n-tetradecyl, n-hexadecyl, n-octadecyl, and n-eicosyl.

The term "alkylene" refers to a functionalized or unfunctionalized divalent straight-chain, branched-chain or cyclic $C_1$-$C_{40}$ group optionally having one or more heteroatoms. Particularly, an alkylene is a $C_1$-$C_{45}$ group and more particularly, a $C_1$-$C_{30}$ group. Particular, yet non-limiting examples of alkylene groups include —$CH_2$—. —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH_2$—$CH_2$—$CH_2$—$CH_2$—$CH_2$—$CH_2$—$CH_2$—, cyclopropylene, cyclobutylene, cyclopentylene, cyclohexylene, and the like.

The term "halogen" refers to chloro, bromo, iodo and/or fluoro.

The term "metal ion" includes alkali metal ions, alkaline earth metal ions, and transition metal ions. For example, sodium, calcium, copper and iron derived ions.

The term "ammonium" includes protonated $NH_3$ and protonated primary, secondary, and tertiary organic amines.

The term "functionalized" refers to the state of a moiety that has one or more functional groups introduced to it by way of one or more functionalization reactions known to a person having ordinary skill in the art. Particular, yet non-limiting examples of functionalization reactions include epoxidation, sulfonation, hydrolysis, amidation, esterification, hydroxylation, dihyroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. Particularly, functionalization of a moiety replaces one or more hydrogens in the moiety with one or more non-hydrogen groups, for e.g., alkyl, alkoxyl, cycloalkyl, alkenyl, cycloalkenyl, alkynyl, and/or aryl groups. Particular, yet non-limiting examples of cycloalkyl groups include cyclopentane, cyclohexane, cycloheptane, and the like. Particular, yet non-limiting examples of alkoxy groups include methoxy, ethoxy, n-propoxy, isopropoxy, and the like. Particular, yet non-limiting examples of aryl groups include benzenes, naphthalenes (2 rings), anthracenes (3 rings), and the like.

The term "monomer" refers to a small molecule that chemically bonds during polymerization to one or more monomers of the same or different kind to form a polymer. The term "homopolymer" refers to a polymer that consists essentially of a single monomer type. The term "non-homopolymer" refers to a polymer that comprises more than one monomer types. The term "copolymer" refers to a non-homopolymer that comprises two different monomer types.

The term "M-06" refers to N-(2-hydroxyethyl)pyrrolidone methacrylate or hydroxyethylpyrolidone methacrylate or Pyrrolidonylethyl methacrylate (PyEMA) and it has synonymously used in this application, the structure of M-06 (CAS NO: 946-25-8) is provided below:

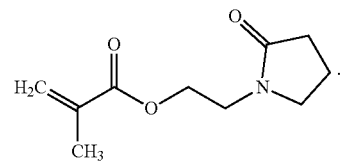

The term "alkyl (alk) acrylate" refers to an alkyl ester of an acrylic acid or an alkyl acrylic acid. The term "alkyl (alk) acrylamide" refers to an alkyl amide of an acrylic acid or an alkyl acrylic acid.

The term "acryloyl" refers to a moiety having the generic structure:

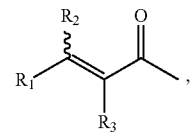

wherein each $R_1$, $R_2$, and $R_3$ is independently selected from the group consisting of hydrogen and functionalized and unfunctionalized alkyl, alkenyl, aryl, nitrile, formyl, carboxyl, carboxylate salt, carboxylic ester, carboxamide, halogen, thiocarboxylate, and combinations thereof The terms "personal care composition" and "cosmetics" refer to compositions intended for use on or in the human body, such as skin, sun, hair, oral, cosmetic, and preservative compositions, including those to alter the color and appearance of the skin and hair.

The phrase "pharmaceutically acceptable" or "cosmetically acceptable" refers to molecular entities and compositions that are generally regarded as safe. Particularly, as used herein, the term "pharmaceutically acceptable" or "cosmetically acceptable" means approved by a regulatory agency of the appropriate governmental agency or listed in the U.S. Pharmacopoeia or other generally recognized pharmacopoeia for use in animals, and more particularly in humans.

The term "turbidity" refers to the cloudiness or haziness of a fluid. The units of turbidity from a calibrated nephelometer are called Nephelometric Turbidity Units (NTU).

The term "hair care composition" refers to any composition intended for use on the human body for protection from harmful or undesirable radiation from the sun.

What is described herein is a personal care conditioning and/or styling composition for a keratin substrate comprising: (A) at least one conditioning and/or styling polymer obtained by polymerizing (i) about 0.1 wt. % to 99.9 wt. % of at least one cationic or pseudo-cationic monomer selected from the group consisting of acrylamidopropyl trimethylammonium chloride (APTAC) and/or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety; (B) at least one cosmetically acceptable excipient; and optionally, at least one effective amount of personal care active ingredient The preferred range of cationic or pseudo-cationic polymer (APTAC/DADMAC) for preparing a desired copolymer of present application include but not limited to 50 wt. % to 55 wt. %; 56 wt. % to 60 wt. %; 61 wt. % to 65 wt. %; 66 wt. % to 70 wt. %; 71 wt. % to 75 wt. %; 76 wt. % to 80 wt.

%; 81 wt. % to 85 wt. %; 86 wt. % to 90 wt. %; 91 wt. % to 95 wt. %. Most preferred range is 86 wt. % to 95 wt. % of the copolymer.

The preferred range of an monomer comprising at least one functionalized or unfunctionalized acryloyl moiety and at least one lactam moiety employed for preparing desired copolymer of present application includes but is not limited to 1 wt. % to 5 wt. %; 6 wt. % to 10 wt. %; 11 wt. % to 15 wt. %; 16 wt. % to 20 wt. %; 21 wt. % to 25 wt. %; 26 wt. % to 30 wt. %. Most preferred range is 1 wt. % to 10 wt. % of the copolymer.

The term "keratin substrate" or "keratinous substrate" as used herein includes skin, nails and "keratin fibers", and wherein the "keratin fibers" means hair on head, eyelashes, eyebrows and other mammalian bodily hair.

The weight average molecular weight of said copolymer of the present application, as determined by gel permeation chromatography (GPC), is at least about 10,000, preferably about 100,000 to about 2,000,000, more preferably from about 200,000 to about 500,000 g/mol, alternatively, viscometry can also be used to determine the average molecular weight of the present application.

The copolymer of use in the personal care composition of the application has a cationic degree of substitution (Cat-DS) of greater than about 0.001 units. Preferably, the copolymer has a cationic degree of substitution in the range of 0.001 to about 5.0, more preferably in the range of from about 0.2 to about 3.0 and more preferably in the range of about 0.4 to about 3.0.

Further, the copolymer of the present application has a cationic charge density in the range of from about 1 meq/g to about 8 meq/g. Preferable cationic charge density is in the range of from about 3.5 to about 7 meq/g, more preferably in the range of about 3.5 to about 5.5 meq/g.

A conditioning and/or styling copolymer of the present application is obtained by polymerizing: (A) (i) about 0.1 wt. % to 99.9 wt. % of at least one cationic or pseudo-cationic monomer selected from the group consisting of acrylamidopropyl trimethylammonium chloride (APTAC) and/or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety; (B) at least one cosmetically acceptable excipient; and optionally, at least one effective amount of personal care active ingredient wherein said co-polymer having a cationic degree of substitution (Cat-DS) of greater than about 0.001 units, and wherein the cationic charge density is in the range of about 1 meq/g to about 6 meq/g.

In a first aspect, the application provides a conditioning and/or styling polymer composition comprising: at least one conditioning and/or styling polymer obtained by polymerizing (i) about 0.1 wt. % to 99.9 wt. % of at least one cationic or pseudo-cationic monomer selected from the group consisting of acrylamidopropyl trimethylammonium chloride (APTAC) and/or diallyl dimethyl ammonium chloride (DADMAC); and (ii) about 0.1 wt. % to 99.9 wt. % of at least one monomer comprising at least one functionalized or unfunctionalized acryloyl moiety and at least one lactam moiety.

In particular, an embodiment, the monomer comprising at least one functionalized or unfunctionalized acryloyl moiety and at least one lactam moiety has a structure:

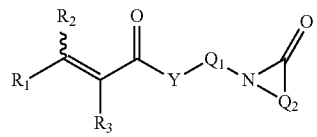

wherein each $R_1$ $R_2$ and $R_3$ is independently selected from the group consisting of hydrogen, halogens, functionalized and unfunctionalized $C_1$-$C_4$ alkyl, and

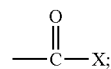

each X is independently selected from the group consisting of $OR_4$, OM, halogen, $N(R_5)(R_6)$,

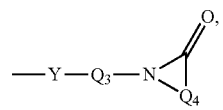

and combinations thereof; each Y is independently oxygen, $NR_7$ or sulfur; each $R_4$, $R_5$, $R_6$ and $R_7$ is independently selected from the group consisting of hydrogen and functionalized and unfunctionalized alkyl; each M is independently selected from the group consisting of metal ions, ammonium ions, organic ammonium cations, and combinations thereof; and each $Q_1$, $Q_2$, $Q_3$, and $Q_4$ is independently selected from the group consisting of functionalized and unfunctionalized alkylene.

Particularly, each $Q_1$, $Q_2$, $Q_3$, and $Q_4$ is independently selected from the group consisting of functionalized and unfunctionalized $C_1$-$C_{12}$ alkylene.

In one non-limiting embodiment, each $R_1$, $R_2$ and $R_3$ is independently selected from the group consisting of hydrogen, methyl and combinations thereof. Particularly, $R_1$ and $R_{22}$ are hydrogens and $R_3$ is hydrogen or methyl.

In another non-limiting embodiment, each $R_1$ and $R_{23}$ is independently hydrogen or methyl; $R_2$ is

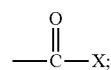

X is selected from the group consisting of $OR_4$, OM, halogens, and $N(R_5)(R_6)$; each $R_4$, $R_5$, and $R_6$ is independently selected from the group consisting of hydrogen and functionalized and unfunctionalized alkyl; and each M is independently selected from the group consisting of metal ions, ammonium ions, organic ammonium cations, and combinations thereof. Particularly, $R_1$ and $R_{23}$ are hydrogens and $R_2$ is

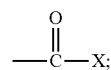

X is selected from the group consisting of $OR_4$, OM and $N(R_5)(R_6)$; each $R_4$, $R_5$, and $R_6$ is independently selected from the group consisting of hydrogen and functionalized and unfunctionalized $C_1$-$C_4$ alkyl; and each M is independently selected from the group consisting of metal ions, ammonium ions, organic ammonium cations, and combinations thereof.

The first polymerizable unit, defined by structure (1), can be synthesized using methods recorded in the art, e.g., by reaction of an N-hydroxylalkyl lactam with an acrylate, (meth)acrylate, anhydride, or similar compounds. Production methods include those described in U.S. Pat. Nos. 2,882,262; 5,523,340; 6,369,163; U.S. Patent Application Publication 2007/123673; GB 924,623; 930,668; and 1,404,989; WO 03/006569; and EP 385918. Each of the previous disclosures are hereby incorporated herein by reference in its entirety.

The lactam-containing monomers shown in structures (2)-(57) can be obtained from condensation reactions that include an N-hydroxyalkyl lactam and an unsaturated carboxylic acid, an acrylate, a (meth)acrylate, or an anhydride. Suitable N-hydroxyalkyl lactams include N-hydroxymethyl pyrrolidone and caprolactam, N-hydroxyethyl pyrrolidone and caprolactam, and N-hydroxypropyl pyrrolidone and caprolactam. Non-limiting examples of carboxylic acids that can be used include: acrylic acid, methacrylic acid, itaconic acid, crotonic acid, fumaric acid, succinic acid, and maleic acid. Similarly, acrylates and (meth)acrylates include (without limitation) methyl, ethyl, butyl, octyl, ethyl hexyl acrylates and their (meth)acrylate analogues. Representative anhydrides include formic anhydride, succinic anhydride, maleic anhydride and acetic anhydride.

In particular embodiments, the monomer having at least one functionalized or unfunctionalized acryloyl moiety and at least one lactam moiety has a structure selected from the group consisting of:

(2)
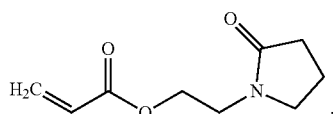

(3)
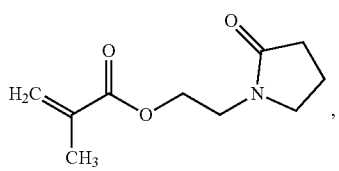

(4)
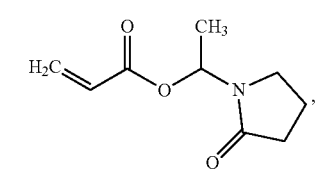

(5)
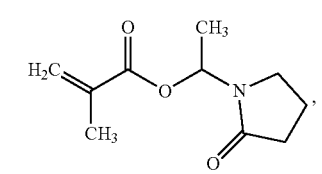

(6)
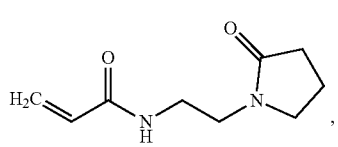

(7)
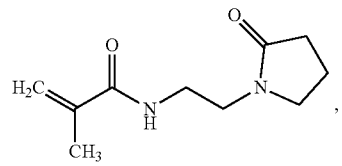

(8)
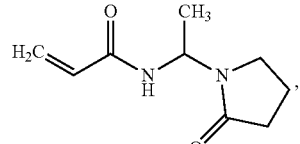

(9)
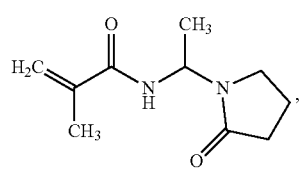

(10)
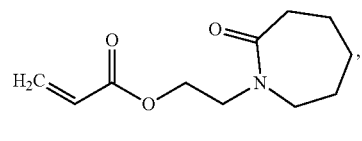

(11)
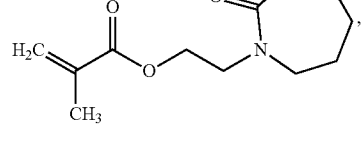

(12)
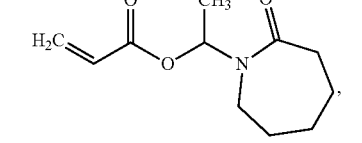

(13)
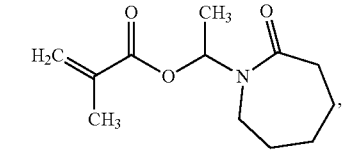

(14)
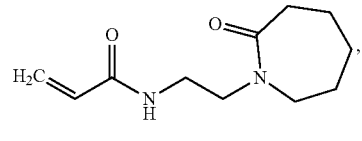

(15)
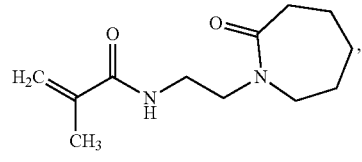

(16)

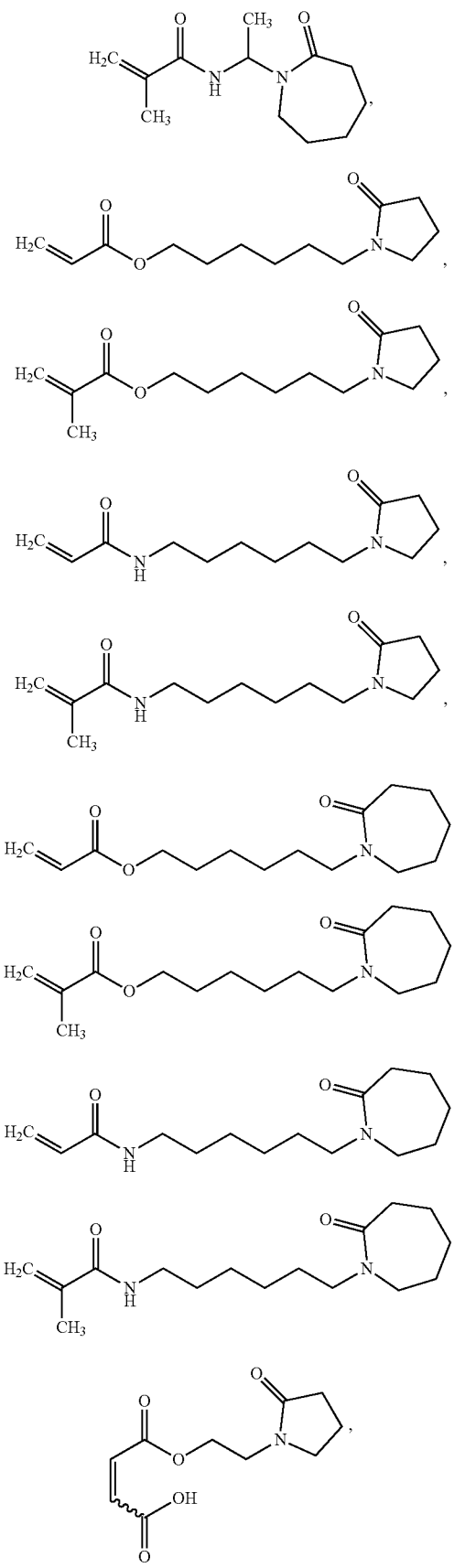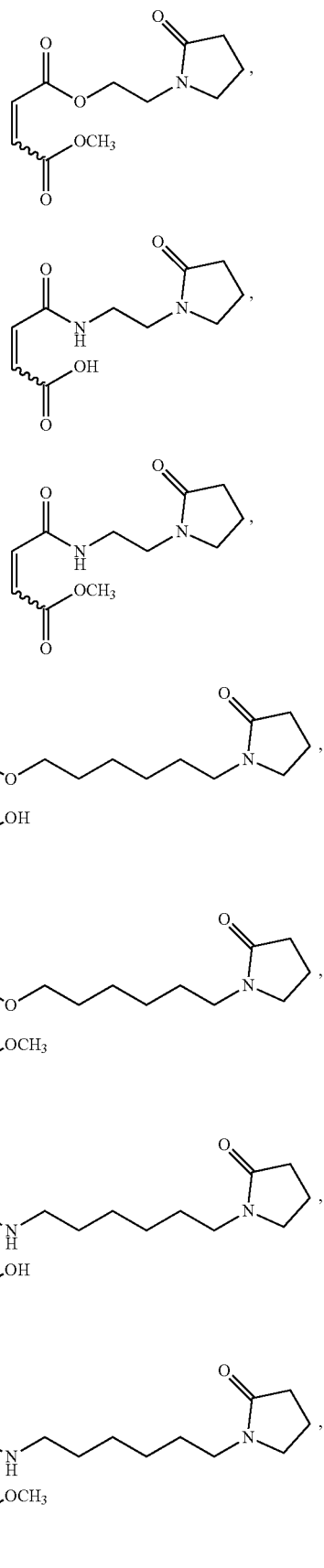

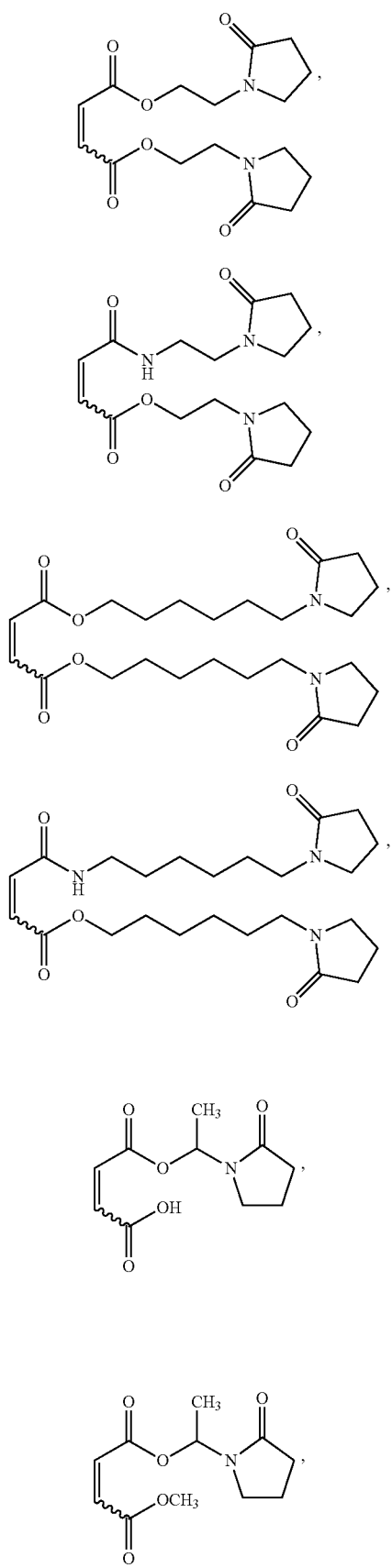
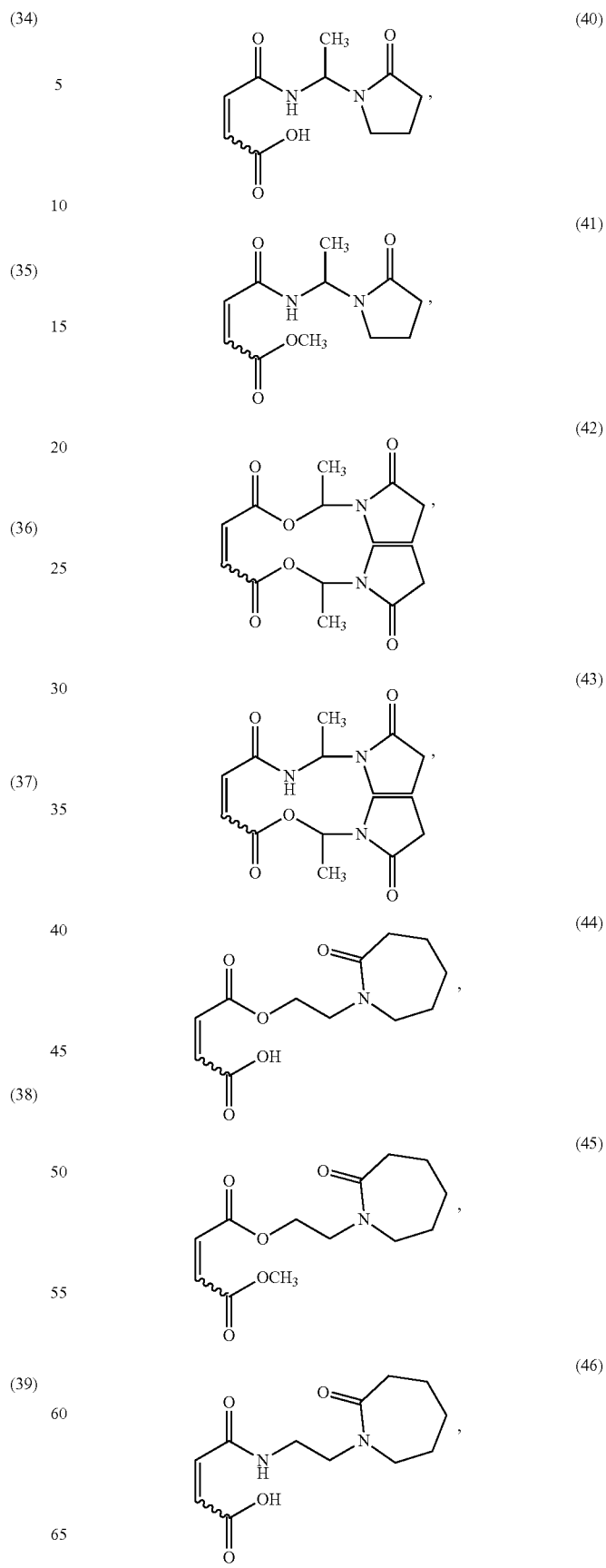

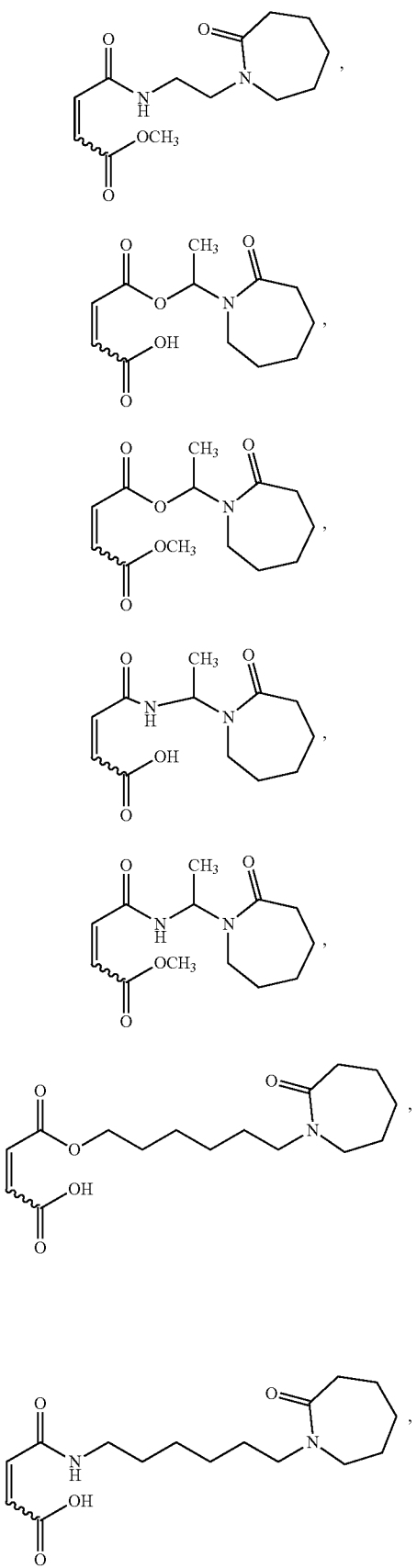
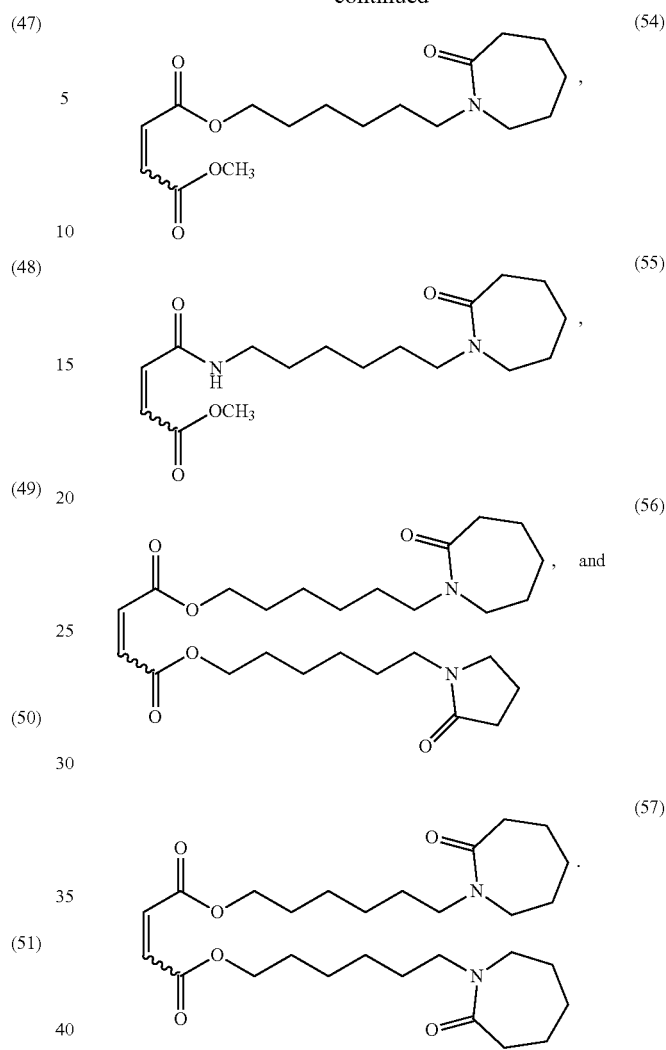

Other suitable examples can be found in WO 2011/063208, the disclosure of which is hereby incorporated herein by reference in its entirety.

In a particular embodiment, it is contemplated to employ (a) about 0.1 wt. % to 99.9 wt. % percent by weight of at least one cationic monomer selected from the group consisting of acrylamidopropyl trimethylammonium chloride (APTAC), diallyl dimethyl ammonium chloride (DADMAC); Acryloyloxyethyltrimethylammonium chloride (AETAC); Methacrylamidopropyltrimethylammonium chloride (MAPTAC); Dimethylaminoethyl methacrylate (DMAEMA or MADAME); Methyloyloxyethyl trimethyl ammonium chloride (METAC); Dimethylaminopropyl-methacrylamideN-(3-chloro-2-hydroxypropyl)trimethylammonium chloride (DIQUAT chloride); and (b) about 0.1 wt. % to 99.9 wt. % percent by weight of at least one functionalized or unfunctionalized acryloyl moiety.

According to one specific embodiment of the present application, wherein the at least one lactam moiety according to the application comprises repeating units derived from at least: from about 0.1 to about 99.9 percent by weight of the polymer of at least one monomer having a structure selected from the group consisting of:

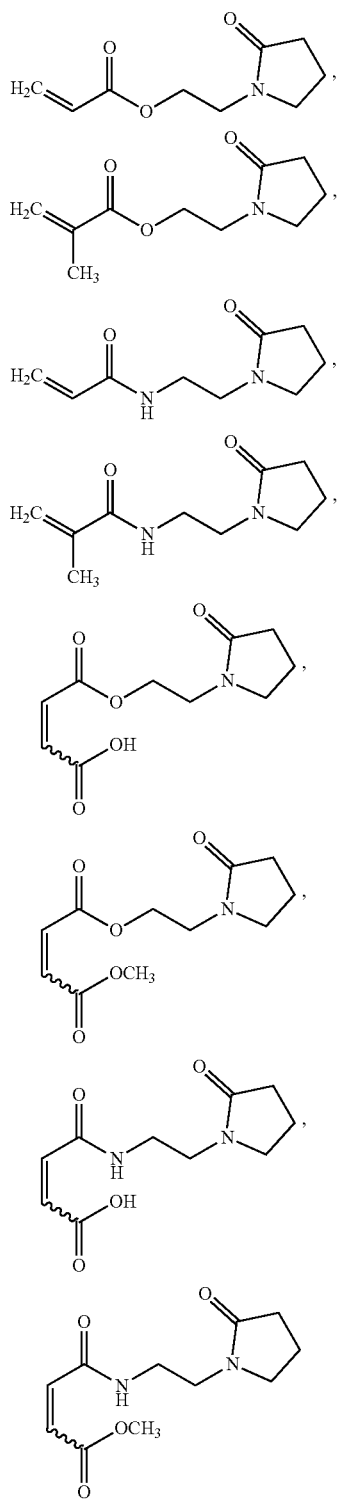

and combinations thereof.

Most particularly, the copolymer comprises functionalized or unfunctionalized acryloyl moiety and at least one lactam moiety repeating units derived from at least: about about 15 to about 25 preferably 20 percent by weight of the polymer of at least one monomer having a structure selected from the group consisting of:

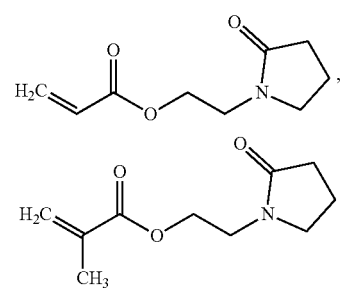

and combinations thereof;

In particular embodiments, the conditioning and/or styling copolymer has a structure selected from the group consisting of:

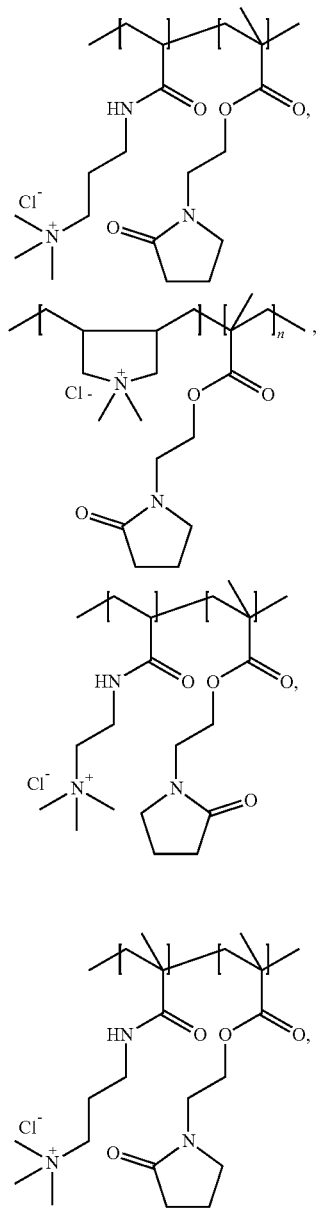

-continued

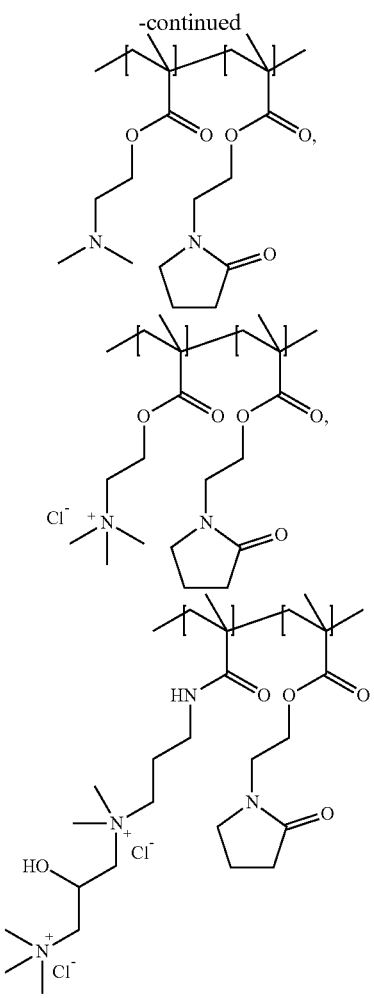

wherein each copolymer is an independently selected value ranging from about 0.1 to about 99.9 percent by weight of the polymer, with the proviso that the sum of cationic or pseudo-cationic monomer and functionalized or unfunctionalized acryloyl moiety for each polymer equals 100 weight percent.

In a particular embodiment, the copolymer (inventive polymer) according to the application further comprises repeating units derived from at least one crosslinker. Non limiting examples of crosslinkers include: divinyl ethers.

The copolymer compositions according to the application may be used as such or formulated with other ingredient(s) resulting in various product forms.

In particular embodiments, the copolymer according to the application is a personal care composition, cementing fluid, oilfield composition, construction composition, servicing fluid, gravel packing mud, fracturing fluid, completion fluid, workover fluid, spacer fluid, drilling mud, coating composition, household, industrial and institutional composition, pharmaceutical composition, food composition, biocide, adhesive, ink, paper, polish, membrane, metal working fluid, plastic, textile, printing composition, lubricant, preservative, agrochemical, or wood-care composition. Particularly, the copolymer composition is a personal care composition, coating composition, household, industrial and institutional composition, pharmaceutical composition, or an agricultural composition. More particularly, the copolymer composition is a personal care composition.

Non-limiting examples of personal care compositions include hair care compositions, sun care compositions, face care compositions, lip care compositions, eye care compositions, skin care compositions, after-sun compositions, body care compositions, nail care compositions, anti-aging compositions, insect repellants, oral care compositions, deodorant compostions, conditioning compositions, color cosmetic compositions, color-protection compositions, self-tanning compositions, and foot care compositions.

The personal care composition of present application is capable of fixing or treating hair and features conditioning and/or styling properties such as detangling, wet combability, wet feel, dry combability, dry feel, sheen, static flyaway control, hydrophobicity, surface smoothening, improved deposition, no build-up, color protection, and/or curl retention. Further, the personal care composition comprising a copolymer of present application is able to provide "virgin feel condition" to the hair after multiple washes.

The personal care composition of present application can be an appropriate product selected from the group consisting of hair-care products, shampoos, hair conditioners, 2 in 1 shampoos, leave in and rinse off conditioners, hair treatments including intensive treatments, styling and treating hair compositions, hair perming products, hair straightners, hair relaxants, hair sprays and lacquers, permanent hair dyeing systems, hair styling mousses, hair gels, semi-permanent hair dyeing systems, temporary hair dyeing systems, hair bleaching agents, permanent hair wave systems, hair setting formulations, non-coloring hair preparations, hair-frizz-control gels, hair leave-in conditioners, hair pomades, hair de-tangling products, hair fixatives, hair conditioning mists, hair care pump sprays and other non-aerosol sprays, skin-care products, hair cuticle coats, skin care moisturizing mists, skin wipes, pore skin wipes, pore cleaners, blemish reducers, skin exfoliators, skin desquamation enhancers, skin towelettes, skin protection ointments, skin powders, skin pads, paste masks and muds, face masks, facial cleansing products, anti-acne preparations, bath products, shower products, liquid soaps, bar soaps, body oils, body lotions, body gels, body and hand preparations, face and body washes, bath salts, bath and body milks, foam baths, synthetic and non-synthetic soap bars, hand liquids, shaving lotions, shaving and aftershave preparations, pre-shaves and pre-electric shaves, nail varnishes, nail polish, nail polish remover, nail creams and lotions, cuticle softeners, nail conditioners, eye shadows, mascaras, eye liners, eye shadows, blushes, makeup, eye shadow sticks, baby lotions, baby baths and shampoos, baby conditioners, fragrances and/or odoriferous ingredients consisting preparations, dentifrices, deodorizing and antiperspirant preparations, decorative preparations, light protection formulations, treatment creams, lipsticks, dry and moist make-up, rouge, powders, depilatory agents, sun care products, compositions comprising UV blockers or UV protectors, anti-aging products, foundations, face powders, moisturizing preparations, tanning preparations, nose strips, make-up removers, cold creams, mousses, shower gels, personal care rinse-off products, gels, scrubbing cleansers, astringents, lip balms, lip glosses, anhydrous creams and lotions, oil/water, water/oil, multiple and macro and micro emulsions, water-resistant creams and lotions, mouth-washes, massage oils, toothpastes, clear gels and sticks, ointment bases, topical wound-healing products, aerosol talc, barrier sprays, vitamin, herbal-extract preparations, and/or controlled-release personal care products. The personal care composition of present application can be formulated in several required forms according to their necessity, and the non-limiting forms include emulsion, lotion, gel, vesicle dispersion, paste, cream, solid stick, mousse, shampoo, spray, balm, wipe, milk, foam, jellies, liquid, tonics, and/or enamel.

The cationic polymers that can be used along with conditioning and/or styling copolymer of this application are those known to improve the cosmetic properties of hair which may be normal or damaged in nature. The expression "cationic polymer" as used herein, indicates any polymer containing cationic groups and/or ionizable groups in cationic groups. The cationic polymers used generally have a molecular weight the average number of which falls between about 500 and 5,000,000 and preferably between 1000 and 3,000,000. The preferred cationic polymers are chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as:

(1) Homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized; the dimethyl amino ethyl methacrylate/vinyl caprolactam/vinyl pyrrolidone terpolymers; the vinyl pyrrolidone/methacrylamidopropyl dimethylamine copolymer; the vinyl pyrrolidone/quaternized dimethyl amino propyl methacrylamide copolymers; and the vinyl pyrrolidone/dimethylaminopropyl methacrylamide/$C_9$-$C_{24}$ alkyldimethylaminopropyl methacrylic acid quaternized terpolymers described in U.S. Pat. No. 6,207,778; (2) Derivatives of cellulose ethers containing quaternary ammonium groups; (3) Derivatives of cationic cellulose such as cellulose copolymers or derivatives of cellulose grafted with a hydrosoluble quaternary ammonium monomer, as described in U.S. Pat. No. 4,131,576; (4) Cationic polysaccharides such as described in U.S. Pat. Nos. 3,589,578 and 4,031,307; (5) Water-soluble polyamino amides prepared by polycondensation of an acid compound with a polyamine. These polyamino amides may be reticulated; (6) Derivatives of polyamino amides resulting from the condensation of polyalcoylene polyamines with polycarboxylic acids followed by alcoylation by bi-functional agents; (7) Polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347; (8) The cyclopolymers of alkyl dialyl amine or dialkyl diallyl ammonium such as the homopolymer of dimethyl diallyl ammonium chloride and copolymers of diallyl dimethyl ammonium chloride and acrylamide; (9) Quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020 (10) Quaternary polyammonium polymers, including; (11) The quaternary polymers of vinyl pyrrolidone and vinyl imidazole; (12) Quaternary polyamines; (13) Reticulated polymers known in the art.

Suitable Polyquaternium type of cationic polymers for the present application would include, but are not limited to, Polyquaternium 4 to Polyquaternium 113. Other cationic polymers that may be used within the context of the application are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

It is contemplated to employ at least one personal care active ingredient for preparing a personal care composition of the present application comprising a conditioner terpolymer and at least one cosmetically acceptable agent, wherein, the preferred personal care active ingredient of the present application would include but not limited to Carnitine, Betain Aminoacids as i.e. valine, glycine, arginine, allantoin, tocopherol nicotinate, niacinamide, retinyl propionate, palmitoyl-gly-his-lys, phytosterol, polyphenolic compounds, flavonoids, flavones, flavonols, isoflavone, dexpanthenol, panthenol, bisabolol, farnesol, phytantriol, salicylic acid, zinc/sodium pyridinethione salts, piroctone olamine, selenium disulfide, tetrahydrocurcumin, glucosamine, N-acteyl glucosamine, vitamin B3, retinoids, peptides, phytosterol, dialkanoyl hydroxyproline, hexamidine, salicylic acid, N-acyl amino acids, escolols, sunscreen actives, UV-A/UV-B protecting agent, UV filters, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), ergothioneine, vanillin, vanillin derivatives, diethylhexyl syrinylidene malonate, melanostatine, sterol esters, fatty acids, poly-unsaturated fatty acids, anti-fungal agents, thiol compounds, N-acetyl cysteine, glutathione, thioglycolate, β-carotene, ubiquinone, amino acids, idebenone, dehydroacetic acid, Licohalcone A, creatine, creatinine, feverfew extract, yeast extract, beta glucans, alpha glucans, alone or in combination.

The effective amount of personal care active ingredient employed in the present application is in the range of from about 0.01 wt. % to about 10 wt. %, preferably about 0.1 wt. % to about 5.0 wt. % and more preferably in the range of 0.05 wt. % to about 3.0 wt. % of the total composition.

As used herein, the term "cosmetically acceptable excipient" means any ingredient/compound or mixture of ingredients/compounds or compositions that are typically employed to produce other desirable effects in personal care compositions.

However, the non-limiting excipients for the present application would include preservatives, antioxidants, chelating agents, sunscreen agents, proteins, amino acids, vitamins, dyes, hair coloring agents, plant extracts, plant derivatives, plant tissue extracts, plant seed extracts, plant oils, botanicals, botanical extracts, humectants, fragrances, perfumes, oils, emollients, lubricants, butters, penetrants, thickeners, viscosity modifiers, thickeners, polymers, resins, hair fixatives, film formers, surfactants, detergents, emulsifiers, opacifying agents, volatiles, propellants, liquid vehicles, carriers, salts, pH adjusting agents, neutralizing agents, buffers, hair conditioning agents, anti-static agents, anti-frizz agents, anti-dandruff agents, hair waving agents, hair straightening agents, relaxers, absorbents, fatty substances, gelling agents, moisturizers, hydrophilic or lipophilic active agent, preserving agents, fillers, dyestuffs, reducing agents, cosmetic oils, perfumes, liquid vehicles, solvents, carriers, silicones, and combinations thereof.

The copolymers according to the application may be readily synthesized by procedures known by those skilled in the art, non-limiting examples of which include free radical solution polymerization, dispersion polymerization, emulsion polymerization, ionic chain polymerization, living polymerization, bulk polymerization, suspension polymerization or precipitation polymerization. Particularly, the polymerization is carried out by any one of the methods disclosed in "Principles of Polymerization" 4$^{th}$ edition, 2004, Wiley by George Odian and is referred and disclosed herein in its entirety and described in "Decomposition Rate of Organic Free Radical Polymerization" by K. W. Dixon (section II in Polymer Handbook, volume 1, 4th edition, Wiley-Interscience, 1999), which is herein incorporated in its entirety by reference.

The copolymers and compositions according to the application may be analyzed by known techniques. Especially preferred are the techniques of $^{13}$C nuclear magnetic resonance (NMR) spectroscopy, gas chromatography (GC), and gel permeation chromatography (GPC) in order to decipher polymer identity, residual monomer concentrations, polymer molecular weight, and polymer molecular weight distribution.

The following examples are presented for purposes of demonstrating, but not limiting, the preparation of the polymers, and wherein, the copolymers include:

PyEMA: Pyrrolidonylethyl methacrylate (CAS Registry Number 946-25-8)
APTAC: Acrylamidopropyltrimethyl-ammonium chloride
DADMAC: Dimethyldiallylammonium chloride
AETAC: Acryloyloxyethyltrimethylammonium chloride
MAPTAC: Methacrylamidopropyltrimethylammonium chloride
METAC: Methyloyloxyethyl trimethyl ammonium chloride
DIQUAT chloride: Dimethylaminopropylmethacrylamide N-(3-chloro-2-hydroxypropyl) trimethyl ammonium chloride Further, certain aspects of the present application are illustrated in detail by way of the following examples. The examples are given herein for illustration of the application and are not intended to be limiting thereof.

EXAMPLES

Example 1: General Polymerization Procedure:
Method for Performing Free Rise Polymerization's in Solution Polymers The resin pot was set up with fitted lid on the required heat source (water bath, oil bath, Huber or isomantle); The resin pot was additionally fitted with a stirrer rod, blade, stirrer gland, water cooled condenser(s), and thermometer or thermocouple and that leads to the required number of peristaltic pumps; the required monomers were weighed out and was poured into the resin pot and heated to the required temperature; The pot contents were stirred throughout the procedure and degas the pot contents with nitrogen for 30 minutes if degassing is required (N.B: The reaction charge may be aqueous and/or alcohol/solvent as dictated by the recipe); When the reaction mixture got stabilized at the required temperature, hold at the required temperature for 30 minutes prior to addition to ensure equilibrium and/or thorough degassing is achieved; The nitrogen bubbler was raised above the surface of the monomer to form a nitrogen blanket; The chain transfer reagent (if required) was added to the monomer; The thermal initiator was also added to the monomer; The reaction mixture was maintained under the set conditions until the polymerization is complete; The reaction mixture was cooled to room temperature and the pot was removed; and the polymer was characterized under the stared specifications (Table 1).

TABLE 1

APTAC/PyEMA at Reaction Temp 55° C. and initiator Vazo and Initiator feed length (hrs) free rise

| Wt % ratio | Experimental conditions | pH | Solids, % (1 g@2 hrs @110° C.) | Turbidity (NTU) | Viscosity, cPs | APTAC residuals (ppm) | PyEMA residual (ppm) | Mw | Pd |
|---|---|---|---|---|---|---|---|---|---|
| 98.2/1.8 | DOE Run 1 98.2/1.8-APTAC:PyEMA. Free rise. | 8.11 | 23.89 | 6.53 | 33000 | 1767 | 37 | 1155000 | 7.67 |
| 90/10 | DOE Run 2 90/10-APTAC:PyEMA. Free rise | 7.95 | 24.30 | 17.58 | 11000 | 1679 | — | 773000 | 5.74 |
| 94.1/5.9 | DOE Run 3 94.1/5.9-APTAC:PyEMA. Free rise | 8.01 | 23.69 | 9.56 | 23000 | 2305 | 35 | 1062000 | 3.3 |
| 90/10 | DOE Run 4 90/10-APTAC:PyEMA. Free rise | 7.93 | 24.16 | 17.07 | 15750 | 2254 | 34 | 832000 | 6.39 |
| 98.2/1.8 | DOE Run 1 98.2/1.8-APTAC:PyEMA. Free rise. | 8.06 | 23.98 | 14.18 | 13500 | 1935 | 29 | 784000 | 7.61 |
| 98/2 | All monomers in pot, free rise polymerisation. 2ME initiator | 7.81 | 23.47 | 16.06 | 14500 | 935 | — | 1042000 | 5.05 |
| 98.2/1.8 | All monomers in pot, free rise polymerisation. pH adjusted to 5 prior to polymerisation. 2ME initiator | 5.25 | 25.55 | 28.01 | 325 | — | — | 170000 | 2.91 |

TABLE 1-continued

APTAC/PyEMA at Reaction Temp 55° C. and initiator Vazo and
Initiator feed length (hrs) free rise

| Wt % ratio | Experimental conditions | pH | Solids, % (1 g@2 hrs @110° C.) | Turbidity (NTU) | Viscosity, cPs | APTAC residuals (ppm) | PyEMA residual (ppm) | Mw | Pd |
|---|---|---|---|---|---|---|---|---|---|
| 92.5/7.5 | Repeat of CS00011-81 | 7.08 | 25.32 | 46 | 10800 | 2370 | | 776000 | 5.67 |
| 92.5/7.5 | Free rise polymerisation, all monomers in pot at 28% solids, 2ME | 6.97 | 28.11 | 4.57 | 31750 | 1416 | <50 | 714000 | 2.73 |
| 90/10 | free rise polymerisation, polymerised at pH 9, 2ME, Post treated with FAS/t-BHP/ascorbic acid | 7.56 | 25.35 | 76.00 | 28500 | 162 | <1 | 1432000 | 3.33 |
| 90/10 | free rise polymerisation, polymerised at pH 5, 2ME, Post treated with FAS/t-BHP/ascorbic acid | 4.83 | 25.40 | 32.21 | 200 | 1.00 | <1 | 127000 | 2.30 |
| 90/10 | free rise polymerisation, polymerised at pH 6, Post treated with FAS/t-BHP/ascorbic acid | 5.91 | 25.76 | 75.00 | 98000 | 16.00 | <1 | 1984000 | 3.55 |
| 92.5/7.5 | free rise polymerisation, polymerised at pH 5, Not post treated | 4.98 | 29.30 | 24.52 | 113000 | 20.00 | <1 | 1819000 | 3.55 |

Results show that it is possible to co-polymerize APTAC/PyEMA via the free rise polymerisation route. The average molecular weight achieved was 127000 to ~2M Da.

Example 2: General Polymerization Procedure: Method for Performing Continuous Addition Polymerization in Solution Polymers The resin pot was set up with fitted lid on the required heat source (water bath, oil bath, Huber or isomantle); The resin pot was additionally fitted with a stirrer rod, blade, stirrer gland, water cooled condenser(s), and thermometer or thermocouple and that leads to the required number of peristaltic pumps; the required monomers were weighed out and was poured into the resin pot and heated to the required temperature; The pot contents were stirred throughout the procedure and degas the pot contents with nitrogen for 30 minutes if degassing is required (N.B: The reaction charge may be aqueous and/or alcohol/solvent as dictated by the recipe); When the reaction mixture got stabilized at the required temperature, hold at the required temperature for 30 minutes prior to addition to ensure equilibrium and/or thorough degassing is achieved. Initial initiator shot, was added, as required prior to commencement of the feeds. The feeds were started immediately using the peristaltic pumps at the required addition rate as stated in the recipe, and wherein, the feeds consisted of monomer feed(s), initiator feed(s) and if required, a chain transfer reagent was fed. The reagents were added at the rate required and maintain the reaction temperature throughout the reaction. Once all the additions are completed, hold the reaction at the required temperature for a further 60 minutes to ensure full reaction has taken place. The reaction mixture was cooled to room temperature and the pot was removed and work up the polymer as the recipe dictates (Table 2).

TABLE 2

DADMAC/PyEMA at Reaction Temp 70° C. and 100° C., initiator Vazo 50
and APS and initiator feed 3.5 and 4

| Wt. % ratio | Experimental conditions | pH | Solids, % (1 g@2 hrs@110° C.) | Viscosity, cPs | DADMAC residuals, % | PyEMA residual | Mw | Pd |
|---|---|---|---|---|---|---|---|---|
| 98/2 | 2% PyEMA as feed (fed in over 1 h 35 mins) DADMAC in pot, 70° C. degas 2 hrs, Vazo 50 fed in over 3.5 hrs | 6.04 | 34.3 | 1700 | 2.1 | <5 ppm | 85650 | 3.96 |
| 95/5 | 5% PyEMA as feed (fed in over 1 hr 35 mins) DADMAC in pot, 70° C. degas 2 hrs, Vazo 50 fed in over 3.5 hrs | 6.22 | 35.99 | 1000 | 2.55 | <5 ppm | 66680 | 4.1 |
| 98.5/1.5 | PyEMA added as solution fed in over 4 hrs, APS 50 ppm fed in over 5 hrs, reaction temp: 100° C. | 6.20 | 42.18 | 2200 | 1.56 | — | 81830 | 4.66 |
| 99/1 | DADMAC and PyEMA in pot, degas 1 hr, reflux at 100° C. 50% solids, 100 ppm/min APS fed over 4 hrs | 7.10 | 40.02 | 5050 | 0.04 | — | 159000 | 2.80 |
| 98/2 | DADMAC and PyEMA in pot, degas 1 hr, reflux at 100° C. 50% solids, 100 ppm/min APS fed over 4 hrs | 6.92 | 40.12 | 10670 | 0.20 | — | 306000 | 5.50 |

TABLE 2-continued

DADMAC/PyEMA at Reaction Temp 70° C. and 100° C., initiator Vazo 50
and APS and initiator feed 3.5 and 4

| Wt. % ratio | Experimental conditions | pH | Solids, % (1 g@2 hrs@110° C.) | Viscosity, cPs | DADMAC residuals, % | PyEMA residual | Mw | Pd |
|---|---|---|---|---|---|---|---|---|
| 97/3 | DADMAC and PyEMA in pot, degas 1 hr, reflux at 100° C. 50% solids, 100 ppm/min APS fed over 4 hrs | 6.24 | 40.39 | 14050 | 0.29 | — | 270000 | 6.30 |
| 95/5 | DADMAC and PyEMA in pot, degas 1 hr, reflux at 100° C. 50% solids, 100 ppm/min APS fed over 4 hrs | 6.90 | 39.88 | 23600 | 0.33 | — | 217000 | 4.20 |
| 90/10 | DADMAC and PyEMA in pot, degas 1 hr, reflux at 100° C. 50% solids, 100 ppm/min APS fed over 4 hrs | 6.95 | 40.25 | 32030 | 0.50 | — | 131000 | 3.40 |
| 99/1 | DADMAC and PyEMA in pot, degas 1 hr, reflux at 100° C. 50% solids, 100 ppm/min APS fed over 4 hrs | 4 | 40.02 | 5050 | 0.04 | — | 159000 | 2.80 |
| 98/2 | DADMAC and PyEMA in pot, degas 1 hr, reflux at 100° C. 50% solids, 100 ppm/min APS fed over 4 hrs | 4 | 40.12 | 10670 | 0.20 | — | 306000 | 5.50 |
| 97/3 | DADMAC and PyEMA in pot, degas 1 hr, reflux at 100° C. 50% solids, 100 ppm/min APS fed over 4 hrs | 4 | 40.39 | 14050 | 0.29 | — | 270000 | 6.30 |
| 95/5 | DADMAC and PyEMA in pot, degas 1 hr, reflux at 100° C. 50% solids, 100 ppm/min APS fed over 4 hrs | 4 | 39.88 | 23600 | 0.33 | — | 217000 | 4.20 |
| 90/10 | DADMAC and PyEMA in pot, degas 1 hr, reflux at 100° C. 50% solids, 100 ppm/min APS fed over 4 hrs | 4 | 40.25 | 32030 | 0.50 | — | 131000 | 3.40 |
| 98/2 | 2% PyEMA as feed (fed in over 1 h 35 mins), DADMAC in pot, 70° C. degas 2 hrs, Vazo 50 fed in over 3.5 hrs | 3.5 | 34.3 | 1700 | 2.1 | <5 ppm | 85650 | 3.96 |
| 95/5 | 5% PyEMA as feed (fed in over 1 hr 35 mins) DADMAC in pot, 70° C. degas 2 hrs, Vazo 50 fed in over 3.5 hrs | 3.5 | 35.99 | 1000 | 2.55 | <5 ppm | 66680 | 4.1 |
| 98.5/1.5 | PyEMA added as solution fed in over 4 hrs, APS 50 ppm fed in over 5 hrs, reaction temp: 100° C. | 5 | 42.18 | 2200 | 1.56 | — | 81830 | 4.66 |

TABLE 3

Shampoo composition

| Content | wt. % | g |
|---|---|---|
| Water | | |
| SLSES | 12 | 44.44 |
| CAPB | 3 | 10.7 |
| APTAC/PyEMA (92.5/7.5) | 0.5 | 0.5 |
| NaCl | 1.2 | 1.2 |
| Citric acid | 0.8 | 0.8 |

Example 3: Wet Comb Energy Measurements

The combing measurement of the hair tresses treated with polymer containing shampoo was performed on Instron device. The energy needed to comb the tress was listed as gf-mm. For every measurement 3 bleached hair tresses were used and the average was calculated. To measure durable conditioning, the tress is first treated with 0.1 g/g hair shampoo, which is then rinsed off and the comb energy is measured. The tress was washed 2 more times and the comb energy was again measured.

Various copolymers comprising APTAC and PyEMA; and terpolymers comprising APTAC/AA/BEM were screened employing Instron Bluehill 3 instrument for evaluating their wet comb energy (FIG. 1), and it was observed that copolymers or terpolymer with PyEMA have demonstrated better results after 1 and 3 washes of hair tresses as compared to control sample having only APTAC homopolymer.

Figure 2:
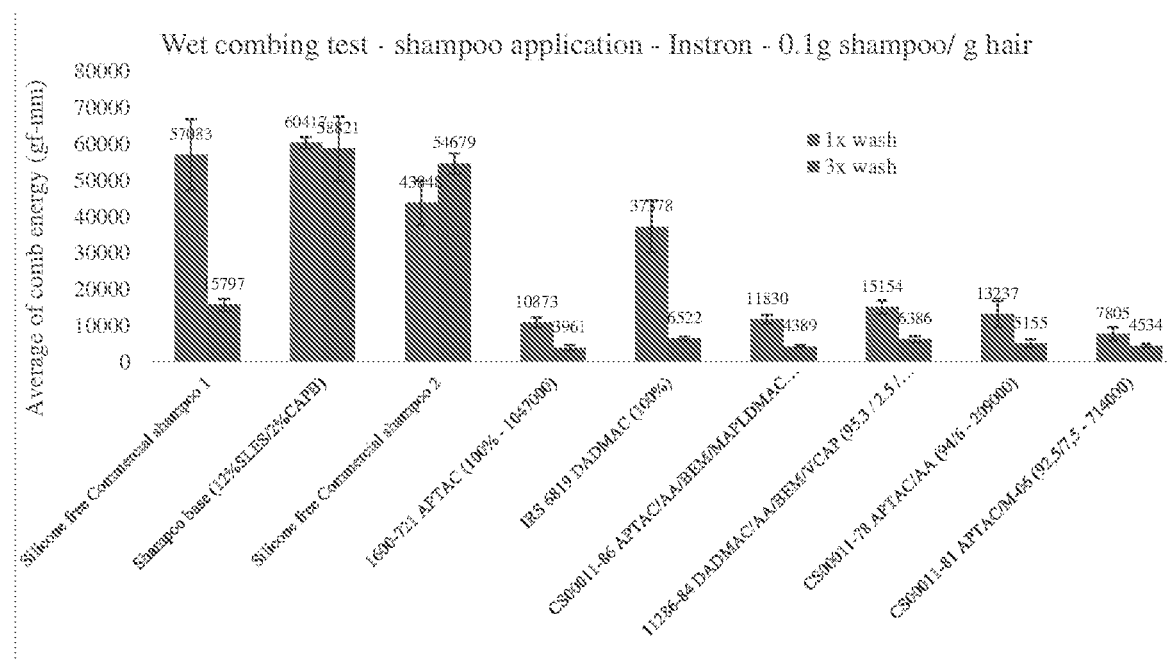
FIG. 2 shows wet combability of copolymers in SLES/CAPB Shampoo formulation.

The copolymers provided improved durability compared to homopolymer/s. Also the initial wet comb energy values right after the application was much lower. From the results (FIG. 2), it is apparent that the combing performance of copolymers after several washes (1 and 3) have demonstrated significantly better performance as compared to commercial available silicone free samples and with shampoo base. Particularly, the APTAC/PyEMA with 92.5/7.5 ratio was capable of providing better result among all other copolymer tested herein. The conditioners were applied on damaged hair 0.2 grams per gram of bleached hair (1 hour bleached) and wet comb energies were measured after 1, 3 and 5 times of washing with 0.1 grams per gram hair shampoo (shampoo: 12/2 SLES/CAPB).

Figure 3:
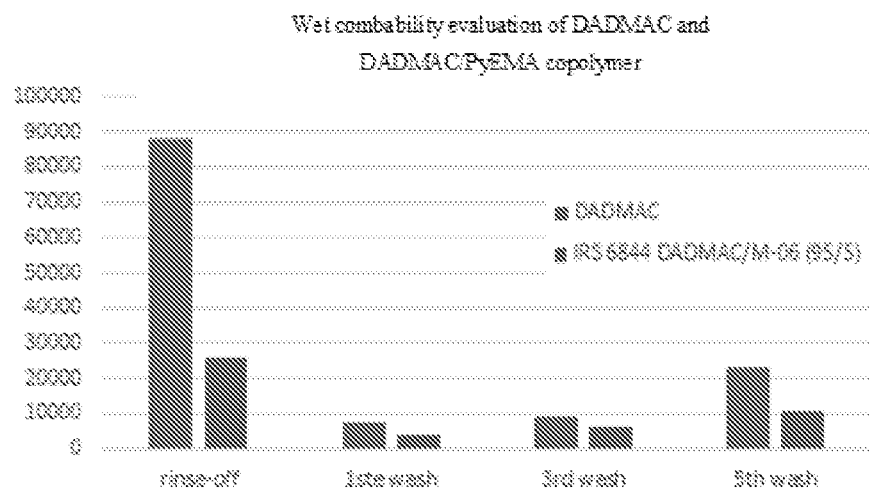
FIG. 3 shows evaluation of DADMAC and DADMAC/PyEMA copolymer.

The PolyDADMAC polymer of Example 3 was hydrophobically modified using 5 wt. % M-06 or PyEMA monomer. The resultant hydrophobically modified polymers was tested as a 1 wt. % in 3% fatty alcohol. As a reference, homopolymer PolyDADMAC was used. The conditioner samples were applied on damaged hair (0.2 g grams per gram of bleached hair, 1 hour bleached) and the wet comb energies of the conditioned hair samples were measured with Texture analyzer after the rinse with water and after 1, 3 and 5 times of washing with 0.1 grams per gram hair shampoo (shampoo: 12/2 SLES/CAPB). The test results are provided in FIG. 3. it was evident that a hydrophobically modified polymer results very low comb energy values showing also excellent long lasting benefits. It is also evident that hydrophobic modification is reducing the initial wet comb energy values compared to the homopolymer.

Example 4: Wet Comb Energy Measurements with Shampoo Applications

Figure 4:
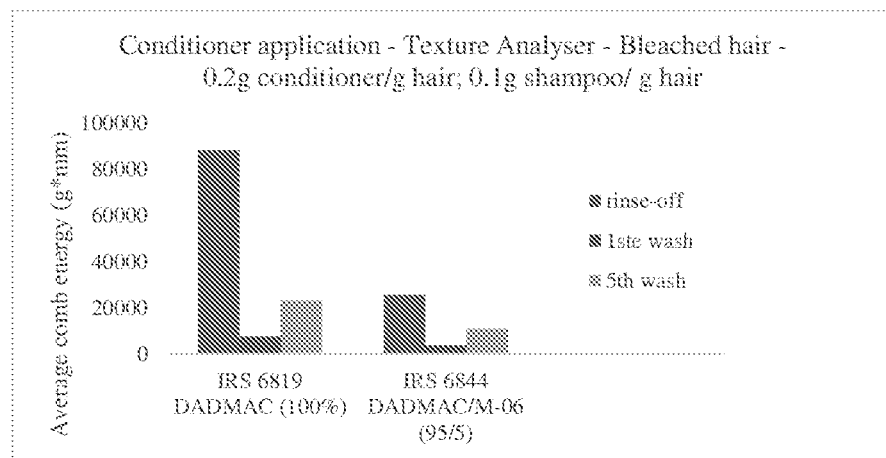
FIG. 4 shows conditioner performance studies for DADMAC and DADMAC/PyEMA copolymer.
Figure 5:
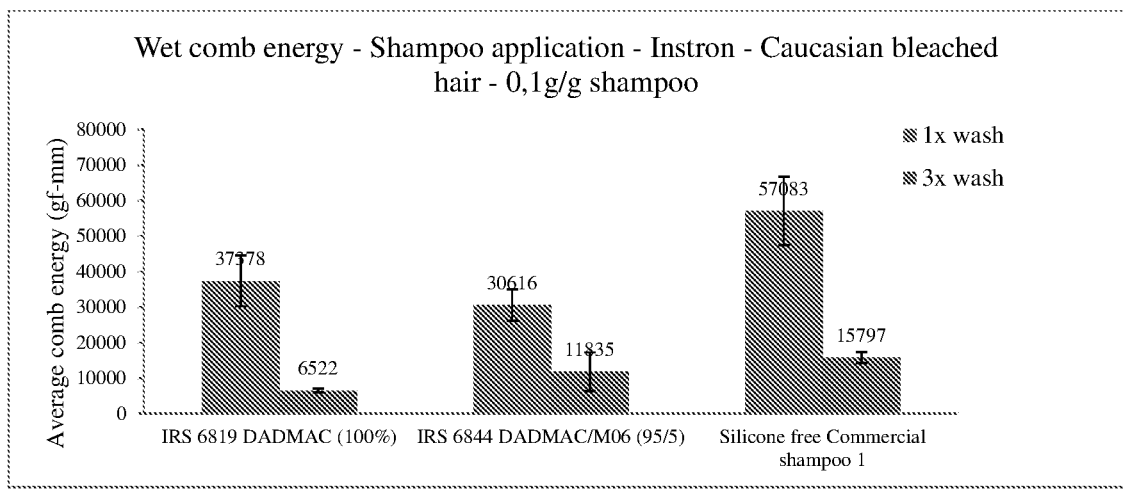
FIG. 5 shows wet comb energy studies for shampoo composition comprising DADMAC based polymers and its comparison to commercial silicone free samples.

The PolyDADMAC and hydrophobically modified PolyDADMAC is also formulated into a surfactant based systems. The resultant hydrophobically modified polymer and homopolymer were tested as a 0.2 wt. % in 12 wt. % SLES 2EO and 2 wt. % CAPB. Conditioning performance was tested using wet comb energy measurements. As a benchmark a Commercial Intensive repair shampoo was used. The test results are provided in FIGS. 4 and 5. From FIG. 5 it was evident that a hydrophobically modified polymer results very low comb energy values. It is also evident that hydrophobic modification is reducing the initial wet comb energy values compared to the homopolymer. Both of the test shampoos are providing improved conditioning performance compared to Commercial Intense repair shampoo.

All of the articles and/or methods disclosed herein can be made and executed without undue experimentation in light of the present disclosure. While the articles and methods of the disclosed and/or claimed inventive concept(s) have been described in terms of particular aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

What is claimed is:

1. A personal care conditioning and/or styling composition for a keratin substrate comprising:
    A. at least one conditioning and/or styling copolymer obtained from polymerizing:
       (i) about 0.1 wt. % to 99.9 wt. % of acrylamidopropyl trimethylammonium chloride (APTAC) or diallyl dimethyl ammonium chloride (DADMAC); and
       (ii) about 0.1 wt. % to 99.9 wt. % of pyrrolidonylethyl methacrylate (PyEMA);
    B. at least one cosmetically acceptable excipient; and
    C. optionally, at least one personal care ingredient;

wherein the at least one copolymer has a cationic charge density in the range of 1 meq/g to 6 meq/g and has a cationic degree of substitution (Cat-DS) of greater than 0.001 units; and wherein said at least one conditioning and/or styling copolymer has a structure selected from the group consisting of:

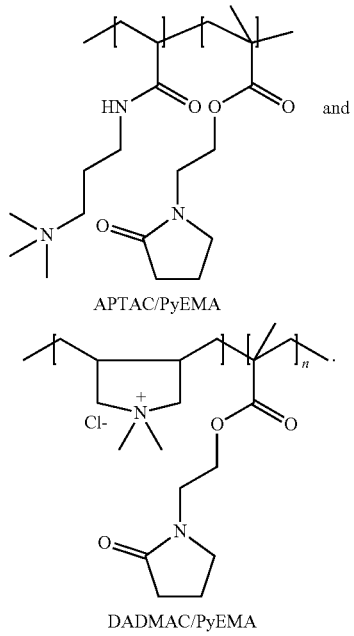

APTAC/PyEMA

DADMAC/PyEMA

2. A method for treating or fixing regular or damaged keratin substrate comprising contacting said keratin substrate with an effective amount of the personal care composition of claim 1.

3. A method for washing or caring for keratin substrate comprising applying an effective amount of the composition of claim 1 to said keratin substrate.

4. A method of protecting dyed hair color from fading or wash-out during exposure to air and/or shampooing which comprises contacting said dyed hair with an effective amount of the personal care composition of claim 1.

* * * * *